United States Patent [19]

Chang et al.

[11] Patent Number: 4,783,571
[45] Date of Patent: Nov. 8, 1988

[54] CATALYTIC CONVERSION OVER DEHYDROXYLATED ZEOLITE

[75] Inventors: Clarence D. Chang, Princeton; Stuart D. Hellring; Richard F. Socha, both of Trenton, all of N.J.

[73] Assignee: Mobil Oil Corporation, New York, N.Y.

[21] Appl. No.: 153,393

[22] Filed: Feb. 8, 1988

Related U.S. Application Data

[63] Continuation-in-part of Ser. No. 944,629, Dec. 19, 1986, Pat. No. 4,724,270, which is a continuation-in-part of Ser. No. 783,269, Oct. 4, 1985, abandoned, which is a continuation of Ser. No. 603,049, Apr. 23, 1984, abandoned.

[51] Int. Cl.$^4$ ............................................ C07C 5/22
[52] U.S. Cl. ............................................ 585/481
[58] Field of Search ............................................ 585/481

[56] References Cited

U.S. PATENT DOCUMENTS

| | | | |
|---|---|---|---|
| 3,097,115 | 7/1963 | Moos | 136/120 |
| 3,939,058 | 2/1976 | Plank et al. | 208/120 |
| 4,016,218 | 4/1977 | Haag et al. | 260/671 |
| 4,060,568 | 11/1977 | Rodewald | 260/682 |
| 4,141,859 | 2/1979 | Plank et al. | 252/455 |
| 4,276,438 | 6/1981 | Chu | 585/467 |
| 4,351,979 | 9/1982 | Chester et al. | 585/481 |

OTHER PUBLICATIONS

Zeolite Molecular Sieves, Donald W. Breck, pp. 493–495, A Wiley–Inter-Science Publication.

Primary Examiner—Curtis R. Davis
Attorney, Agent, or Firm—Alexander J. McKillop; Michael G. Gilman; Malcolm D. Keen

[57] ABSTRACT

The acidity of a zeolite catalyst is reduced by calcination in an essentially water-free atmosphere at temperatures above 700° C., preferably from 725° to 800° C., to reduce the alpha value to less than 10 percent of its original value. The low acidity catalysts produced in this way may be used for isomerizing alkyl di-substituted aromatic compounds, especially xylenes, to products containing higher proportions of the para-isomers.

12 Claims, 1 Drawing Sheet

FIGURE 1. META XYLENE ISOMERIZATION OVER HTC-ZSM-5

CATALYTIC CONVERSION OVER DEHYDROXYLATED ZEOLITE

CROSS REFERENCE TO RELATED APPLICATIONS

This application is a continuation-in-part of patent application Ser. No. 944,629, filed Dec. 19, 1986, now U.S. Pat. No. 4,724,270, which was, in turn, a continuation-in-part of Ser. No. 783,269, filed Oct. 4, 1985, now abandoned, which was itself a continuation (FWC) of Ser. No. 603,049, filed Apr. 23, 1984, now abandoned. The disclosures of those applications are incorporated in the present application by this reference to them.

FIELD OF THE INVENTION

This invention relates to a process for preparing low acidity zeolites and the use of such zeolites in catalytic conversions of aromatic hydrocarbons which are effectively carried out in the presence of low acidity catalysts.

BACKGROUND OF THE INVENTION

Zeolitic materials, both natural and synthetic, are known to have the capability for catalyzing various types of hydrocarbon conversion reactions which take place in the presence of catalytic sites with acidic functionality. These zeolite materials generally have ordered, porous crystalline structures within which there are a number of small cavities that are interconnected by a number of still smaller channels. These cavities and channels are precisely uniform in size within a specific zeolitic material. Since the dimension of these pores are such as to accept for adsorption purposes molecules of certain dimensions, while rejecting those of larger dimension, these materials have commonly been known to be "molecular sieves" and are utilized in a variety of ways to take advantage of the adsorptive properties of these compositions. The structures may be determined by X-ray diffraction techniques.

Ths molecular sieves include a wide variety of positive ion-containing crystalline aluminosilicates and other siliceous materials such as borosilicates, ferrosilicates and gallosilicates in which the presence of the trivalent metal at sites within the silicate structure provides the desired acidic functionality in an environment which permits access to the site only by molecules of appropriate size so that the acid catalyzed reactions are carried out in a "shape selective" manner. Metal cations such as sodium which are usually present in these materials when they are synthesized may be converted to the hydrogen form by exchange with ammonium ions followed by heating to drive off ammonia or by direct exchange with an acid such as hydrochloric acid, if the zeolite is not degraded by the acid. Useful catalysts are also produced by a combination of ion-exchange treatments in which the crystalline silicate may be converted to the acid form and then may be ion exchanged with a solution of various metal salts to produce the metal exchanged zeolite.

The acid activity of aluminosilicate zeolites may be so high that conventional hydrocarbon conversion processes and apparatus cannot take full advantage of this high activity. For example, in catalytic cracking, high activity may yield excessive coke formation and the production of large anions of light gases. The acid activity of zeolite catalysts may, however, be lowered to a level at which the use of such catalysts in catalytic conversions is satisfactory and, in fact, results in a considerable increase in the efficiency of such processes. Reactions which have been performed successfully over low acidity zeolites, especially the intermediate pore size zeolites, include the conversion of oxygenates such as methanol and dimethyl ether to olefin and other hydrocarbon products, xylene isomerization, aromatic alkylation, and olefin oligomerization, as well as catalytic dewaxing and hydrodewaxing and hydroisomerization. The intermediate pore size zeolites have also achieved significant utility in the processing of aromatics, especially in the production of para-disubstituted benzenes such as p-xylene and p-ethyltoluene. Processes of this kind are described in Catal. Rev.—Sci. Eng. 28 (283), 185–264 (1986), especially 249–254, to which reference is made for a description of such processes. Typical xylene isomerization processes are disclosed in U.S. Pat. Nos. 3,856,872; 4,101,595; 4,101,596, 4,101,597; 4,163,028; Re 30157 (3,856,873); Re 31919 (4,312,790); 4,385,195; 4,224,141 and 3,856,871. Aromatics alkylation is disclosed in U.S. Pat. Nos. 3,755,483; 4,086,287; 4,117,024 and 4,117,026. Reference is made to these disclosures for descriptions of such processes.

One method of reducing the activity of aluminosilicate zeolite catalyst is by compositing the zeolite with a matrix material which is relatively inactive. Suitable matrix materials include inorganic oxides, such as those of silica, zirconia, alumina, magnesia and combinations of such materials with one another, as well as clays and other refractory materials.

Other methods to reduce the activity of acid zeolites include cation exchange with sodium or other alkali metal cations or by forming the zeolites with high silica:alumina mole ratios in the structure or framework. An important method in reducing the activity of zeolite catalysts is by a process of steam treating. By control steaming, it is possible to produce zeolite catalysts having any desired degree of activity. The degree of steaming of a specified catalyst to achieve a desired activity level is largely dependent upon the nature of the zeolite. Steam treatment, however, often requires long periods of time to treat the catalyst effectively for activity reduction.

U.S. Pat. No. 3,939,058 discloses methods of modifying the catalytic properties of zeolites. One such method is calcination which is defined as heating at high temperatures but below the sintering temperature of the zeolite for varying periods of time. Other methods are also disclosed, including compositing the zeolite in a matrix and steam treatment. The patent further discloses that the crystallinity retention of catalysts may be improved by precalcination of the crystalline aluminosilicate. For example, the patent states that it has been found possible to preserve the crystallinity of aluminosilicates such as the rare earth exchange synthetic faujasites, by calcining the zeolite to drive off water, thus forming a more suitable structure and minimizing loss in crystallinity during subsequent rapid drying, as in spray drying, wet processing, steaming and aging. The calcining may be accomplished by heating the crystalline aluminosilicate sieve atter ion exchange to a temperature below the sintering temperature of the sieve and generally in the range of from 500° to 1600° F. (about 260° to 870° C.).

Similarly, U.S. Pat. No. 4,141,859 discloses a method of controlling the relative acid activity of zeolite catalysts, by treating the zeolitic component with air or steam at elevated temperatures, e.g., up to 1700° F. (about 925° C.) in air or at temperatures from about 800° F. to about 1700° F. (about 425° C. to 925° C.).

Calcination of the freshly synthesized zeolite to remove adsorbed water and organic materials that have been used to form the zeolite crystals is necessary to activate the zeolite and accordingly has generally been employed. Also, as stated above, precalcination of the zeolite has been found to stabilize the crystallinity of the zeolite. However, heat treatment may remove hydroxyl groups from the framework of the zeolite. Thus, dehydroxylation of a decationized Y zeolite is discussed in *Zeolite Chemistry and Catalysts*, ACS Monograph 171, pages 142 and 143, in which dehydroxylation of Y zeolite is stated to result from prolonged calcination at relatively high temperatures, resulting finally in the structural collapse of the zeolite and the formation of an amorphous silica or silica-alumina structure. For these reasons, the use of high temperatures has generally been avoided in zeolite synthesis. When organic materials are to be removed from the freshly synthesized zeolite, temperatures of about 1000° F. (about 540° C.) are typical and generally not exceeded in order to avoid damage to the crystal structure.

Calcination or high temperature treatment has been employed in various catalyst treatments to achieve particular results, for example, to convert impregnated metal or other compounds to different forms as described in U.S. Pat. Nos. 4,276,438 and 4,060,568 or to destroy ion exchange capacity as described in U.S. Pat. No. 3,0997,115. However, even in such cases the use of higher temperatures, e.g. above 500° C., has not been preferred because of the undesirable effect on the structure of the zeolite.

SUMMARY OF THE INVENTION

In accordance with the present invention, the acid activity (as typically measured by the alpha scale) of intermediate pore size zeolites such as ZSM-5 can be reduced by calcining the zeolites in the absence of water at temperatures greater than about 600° C. but less than the temperature at which the crystallinity of the zeolite collapses. It has been found that the alpha activity of these zeolites can be reduced to less than 10% of the initial alpha value by the high temperature treament. The resultant low acidity catalysts can be used effectively in catalytic conversions in which low acidity zeolite catalysts are effective to catalyse the conversion reaction. The high temperature treatment to reduce the alpha activity of the present invention takes less time and may yield a more stable catalyst than steam deactivation.

The high temperature calcination (HTC) treatment materially improves the properties of the zeolite, especially its selectivity for the production of para-disubstituted aromatic compounds such as the para-dialkyl benzenes e.g. p-xylene. The selectivity is notably better than that of zeolites of comparable acidity produced by steaming or other procedures.

According to the present invention there is therefore provided a process for converting a hydrocarbon feed containing aromatic compounds to a product including substituted aromatic compounds by contacting the feed with an intermediate pore size zeolite (Constraint Index —1-12, silica:alumina ratio at least 12:1) which has been subjected to calcination in a substantially dry atmosphere at a temperature of at least 700° C. to reduce the acidity of the zeolite to an alpha value below 100. Reactions which may be effected in this way include the isomerization of xylene isomers to product enriched in p-xylene, aromatics alkylation and the like.

Other hydrocarbon conversion reactions where improved selectivities to desired products are noted include the olefin oligomerisation, catalytic dewaxing and hydrodewaxing (where improved selectivity of removal of straight and slightly branched chain paraffins may be secured), paraffin hydroisomerisation and conversion of oxygenates to hydrocarbons, as disclosed in Ser. No. 944,629 (U.S. Pat. No. 4,724,270).

BRIEF DESCRIPTION OF DRAWING

The drawing graphically shows the para-selectively resulting from the use of various catalysts.

DETAILED DESCRIPTION

Figure 1:
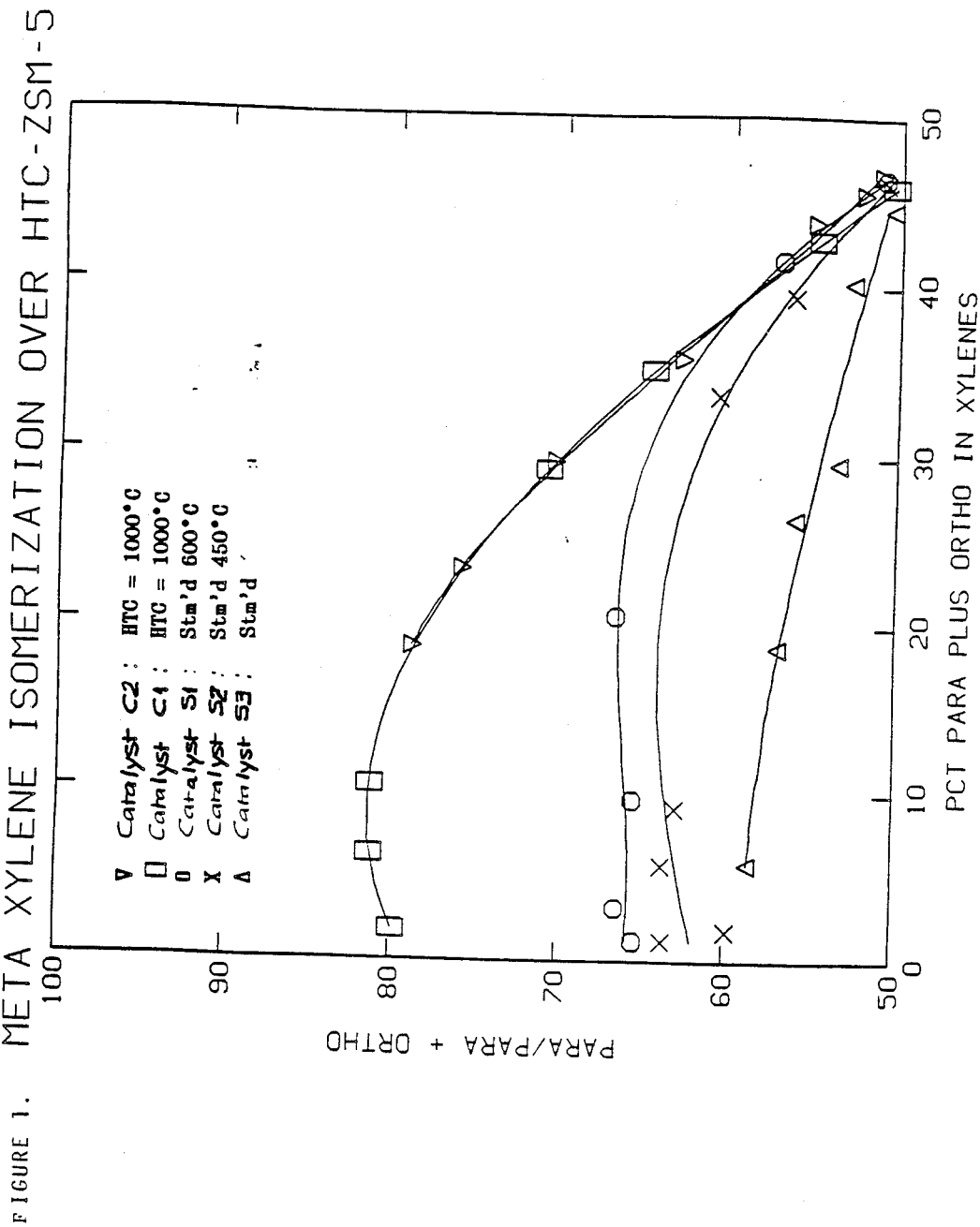

In accordance with the present invention, the alpha activity of a catalyst comprising a crystalline aluminosilicate zeolite having a silica-to-alumina ratio of at least about 12 and a Constraint Index within the approximate range of 1 to 12 can be reduced by heat treating the zeolite at temperatures of 600° C. and above, preferably above 700° C. Non-limiting examples of crystalline aluminosilicate zeolites that can be effectively treated in accordance with this invention include ZSM-5, ZSM-11, ZSM-12, ZSM-23, ZSM-35, ZSM-38, ZSM-48 and zeolite beta.

The synthesis and characteristics of zeolite ZSM-5 are described in U.S. Pat. No. 3,702,886; of zeolite ZSM-11 in U.S. Pat. No. 3,709,979; of zeolite ZSM-12 in U.S. Pat. No. 3,832,449 of zeolite ZSM-23 in U.S. Pat. No. 4,076,842; of zeolite ZSM-35 in U.S. Pat. No. 4,016,245; of zeolite ZSM-38 in U.S. Pat. No. 4,406,850 and of zeolite ZSM-48 in U.S. Pat. No. 4,397,827.

These above-defined zeolites can function as catalysts even when modified to have low alpha values, typically less than 10, and even at alpha values substantially lower than 1. As noted above, low acid activity has previously been achieved by using zeolites of very high silica/alumina ratio, extensive ion exchange of the zeolite with sodium or other alkali metal cations, or by severe temperature steaming of zeolites.

In accordance with the present invention, the alpha activity of the above-defined zeolites is reduced by calcining the zeolites at high temperatures, above 600° C., preferably above 700° C., in an essentially water-free atmosphere (although minor, non deleterious amounts of water may be present).

Alpha activity is an approximate indication of the catalytic cracking activity of the catalyst compared to a standard catalyst. Alpha is the relative rate constant (rate of n-hexane conversion per unit volume of oxides, compositions per unit time). It is based on the activity of highly active silica-alumina cracking catalyst taken as alpha=1 (12.5% cracking at 5 minutes on stream). Alpha activity is further defined in U.S. Pat. No. 3,354,078 and the *Journal of Catalysis*, 4, 522-529, (August, 1965) and J. Catal. 6 278 (1966). Alpha values reported here are determined at a fixed temperature at 538° C., as described in J. Catal. 61, 395 (1980). The Constraint Index of a zeolite may be determined by the method described in U.S. Pat. Nos. 4,016,218 and 4,696,732.

Generally, ZSM-5 and other intermediate pore size zeolites having a Constraint Index of 1-12 are activated by calcining the zeolite at temperatures of about 550° C. to remove water and organic directing agents which are typically included in the synthesis mixture from which the zeolite is made. In accordance with present invention, however, the zeolites are treated above 600° C. and preferably at temperatures from 700° to 800° C. (but less than the sintering temperature of the zeolite) to reduce the acid activity of the zeolite. Significant dehydroxylation does not commence at least until 700° C. or higher temperatures. The temperature should therefore be above 700° C., preferably above 725° C. although normally temperatures above 800° C. will not be preferred both for reasons of convenience (special high temperatures equipment will be needed at higher temperatures) and because dehydroxylation has been found to occur most rapidly in the range between 700° C. and 800° C. Although the temperature required for reducing the alpha activity may vary between the individual zeolites the treatment temperature should generally not exceed 1100° C., above which temperature the structural framework begins to collapse.

Calcination is achieved by heating the zeolite at the desired elevated temperature, in dry air, hydrogen or an inert gas such as nitrogen. Typically, the heat treatment proceeds for at least 1 hour, although heating may last between 1-24 hours. The heat treatment is dry (no water), although up to 2% by weight steam may be included in the calcining atmosphere.

It is theorized that at the high temperature used for achieving reduced alpha activity, removal of framework hydroxyl groups is taking place (i.e. dehydroxylation). The heat treatment should not continue beyond the point at which crystallinity of the zeolite is lost. Typically, at least 55% of the crystallinity of the zeolite will be maintained under the heat treatment conditions. However, catalytic activity and selectivity to desired products may be enhanced in spite of the decrease in acid activity, as measured by the alpha value.

The final alpha value of the zeolite is typically below 50 and in many cases below 10. Alpha values even lower than this may nonetheless be possessed by catalytically useful materials in reactions requiring only a limited degree of acidity. Alpha values of this low order of magnitude i.e., 10 or less, have been formed to be highly effective for the isomerisation of dialkyl substituted aromatics to products containing enhanced proportions of the para-disubstituted isomer.

The reactions which may be catalysed by the zeolites treated in this way are those in which a feed is subjected to an acid-catalysed conversion by means of the solid, zeolite catalyst. The acidic sites at which the catalytic reaction mechanisms take place are found within the porous internal structure of the zeolite where access to these sites may be gained by the reactants. The porous structure of the zeolite may also impede egress by the reaction products and therefore it is necessary, if the reaction is to occur, that the reaction products should also be able to leave the pore structure of the zeolite after the catalytic mechanisms have taken place.

The feed for the process comprises an alkyl di-substituted aromatic, usually a xylene although other substituted aromatics may also be treated by the present process using the HTC zeolite catalysts e.g. cresol and other substituted phenols, haloaromatics e.g. methyl chlorobenzene etc. The alkyl substituents will normally be lower alkyl ($C_1$-$C_6$), usually methyl, ethyl or other linear, lower alkyl groups which can pass through the pore openings of the intermediate pore size zeolites. In the feed, the proportion of the para-substituted (1,4-) isomer is less than the equilibrium amount but the effect of the isomerization process is to increase the proportion of the para-isomer to more than the equilibrium amount. The process is particularly useful for increasing the proportion of para-xylene in petrochemical process streams containing the isomeric xylenes i.e. o-, m-, p-xylenes. The content of the m-isomer is reduced to very low levels in favor of the more valuable p-isomer.

The xylene isomerization process is carried out at elevated temperature, typically at least about 500° F. (about 260° C.) and usually above about 600° F. (about 315° C.). Temperatures are usually in the range of 600°-800° F. (about 315°-425° C.) with pressures typically up to about 1000 psig (about 7000 kPa abs.). The processes described in U.S. Pat. Nos. 030,157 (3,856,873) and 4,101,596 which operate at low pressures in the absence of hydrogen, typically up to about 50 psig (about 446 kPa abs.) employ temperatures which are raised in the course of the cycle to maintain catalyst activity, typically from about 600° F. (about 315° C.) to about 800° F. (about 425° C.). At higher pressures e.g. up to about 400 psig (about 2860 kPa abs.) temperatures of about 600°-650° F. (about 315°-345° C.) are useful. A high temperature isomerization process is described in U.S. Pat. Nos. Re. 31,919 (4,312,790) and 4,385,195 typically using temperatures up to about 900° F. (about 480° C.). If hydrogen is used, the hydrogen:xylene (feed) ratio is typically at least 1:1, usually about 3:1-10:1. The zeolite catalyst may contain a hydrogenation component, typically a metal of Group VIIIA of the Periodic Table (IUPAC Table), such as nickel or platinum. Space velocities are relatively high, usually at least 5 WHSV or higher, typically 6-10 WHSV or even higher in the case of the high temperature process. The feed, in all cases, comprises a mixture of the isomeric xylenes, possibly with impurities including aromatics ($C_{9+}$). The product will include higher proportions of the para-isomer produced by the isomerization process, in relative amounts greater than the equilibrium concentration.

Reference is made to the patents identified above for detailed descriptions of such isomerization processes. The present heat-treated zeolites may be used in the same way in those processes as the zeolite catalysts described in those patents except that enhanced para-selectivity may be noted as compared to the corresponding steamed zeolites.

The following Examples illustrate the invention. All samples of the thermally deactivated ZSM-5 produced in Examples 1-4 originated from the $NH_4$ form ZSM-5 ($SiO_2/Al_2O_3=70$), which had been converted into the proton(H)-form by calcination 1° C./min. to 538° C., then held 10 hr., alpha=214.

EXAMPLE 1

An HZSM-5 sample was calcined at 800° C. for 1 hour, then at 1000° C. for 1 hour (alpha=0.4).

EXAMPLE 2

An HZSM-5 sample was calcined at 1000° C. for 1 hour, (alpha=0.9).

EXAMPLE 3

An HZSM-5 sample was calcined at 800° C. for 1 hour, (alpha=12). A mixture of this zeolite (65%) in $Al_2O_3$ was used.

EXAMPLE 4

An HZSM-5 sample, as a mixture (65%) in Al$_2$O$_3$, was calcined at 1038° C. for 16 hours (alpha=0.1).

EXAMPLE 5

The conversion of m-xylene over the thermally treated ZSM-5 of Example 2 (alpha=0.9) is shown in Table 1 below.

TABLE 1

| | | |
|---|---|---|
| LHSV | 6.8 | 1 |
| Temperature, °F. (°C.) | 427 (220) | 427 (220) |
| Pressure | 150 | 150 |
| Time on Stream (Hours) | 0.5 | 4.5 |
| | Feed | | |
| % Products | | | |
| Toluene | — | 0.08 | 0.95 |
| p | 0.14 | 8.49 | 23.35 |
| m    Xylene | 99.86 | 87.59 | 58.81 |
| o | — | 3.51 | 15.46 |
| C$_9$+ Aromatics | — | 0.25 | 1.429 |
| Normalized Xylenes | | | |
| p | — | 8.52 | 23.92 |
| m    Xylene | — | 87.95 | 60.24 |
| o | — | 3.51 | 15.84 |
| p-Xylene % Equilibrium* | — | 36.3 | 101.8 |
| % m-Xylene Converted | — | 12.27 | 41.05 |

*Xylenes equilibrium at 427° C.: 23.5 para, 52.1 meta, 24.4 ortho.

EXAMPLE 6

Table 2 illustrates xylene isomerization over thermally deactivated ZSM-5.

TABLE 2

| | | |
|---|---|---|
| Catalyst (α) | 0.9 | 0.2 |
| Pressure (psig) | 150 | 150 |
| Temperature, °F. (°C.) | 800 (427) | 800 (427) |
| LHSV | 6.8 | 1 |
| Time on Stream (Hours) | 3 | 2 |
| Products wt. % | Feed | | |
| Benzene | — | 0.15 | 1.56 |
| Toluene | — | 0.06 | 1.03 |
| Ethylbenzene | 14.79 | 14.02 | 11.38 |
| para | 0.24 | 7.25 | 19.51 |
| meta   Xylene | 84.41 | 75.38 | 54.89 |
| ortho | 0.56 | 2.29 | 9.23 |
| C$_9$+ Aromatics | — | 0.85 | 2.40 |
| Normalized Xylenes | | | |
| para | | 8.54 | 23.33 |
| meta   Xylene | | 88.77 | 65.63 |
| ortho | | 2.70 | 11.04 |
| para-Xylene % Equilibrium* | | 36.3 | 99.3 |
| % m-Xylene Conv. | | 10.7 | 35.0 |
| % Ethylbenzene Conv. | | 5.3 | 23.1 |

*Xylenes equilibrium at 427° C., p-xylene 23.5, m-xylene 52.1, o-xylene 24.4

EXAMPLE 7

ZSM-5 (5 g. silica:alumina=72, alpha 538° C.=179) was calcined in a box furnace under flowing nitrogen by heating at 21° C. min$^{-1}$ to 1000° C. then folding for 1 hour at 1000° C. The sample was removed from the furnace and rapidly cooled under a blanket of flowing argon. The product (silica:alumina=289, alpha 538° C.=6.8) was used for the isomerization of meta-xylene as described below.

A small portion of this sample (1 g) was exchanged with aqueous ammonium hydroxide (1M overnight at room temperature after being treated with ammonia gas. Temperature programmed ammonia desorption (TPAD) indicated that the sample had a silica/alumina ratio of about 290.

This HTC-ZSM-5 sample identified as Catalyst C1 was pelleted, meshed (14/30), then loaded (1.20 g, 3 ml) into a stainless steel reactor and heated under flowing nitrogen to reaction temperature (426° C., 150 psig). Meta-xylene was pumped as liquid (undiluted) at varying flow rates to obtain a range of conversions.

For comparison purposes, the same ZSM-5 parent (silica:alumina—72) was treated with flowing steam (water partial pressure=1 atm) at 600° C. for 13.5 hours. The product had an acidity comparable to that of the HTC zeolite (alpha=6.1); TPAD showed a silica:alumina ratio of 250:1. The steamed ZSM-5 sample (catalyst S1:1.23 g. 3 ml) was used for xylene isomerizaton under the same conditions as described above.

The results are given in Table 3 below and graphically in FIG. 1. FIG. 1 shows that para-selectivity rises below about 48% conversion, to give 80% para-selectivity at 20% conversion (99.9% xylenes in product) for the HTC zeolite. The HTC zeolite gives a significant advantage in para-selectivity at conversion levels between about 30 and 60 percent. The steamed zeolite shows 65% para-selectivity at 20% conversion (99.9% xylenes in product).

TABLE 3

META-XYLENE ISOMERIZATION OVER ZSM-5 (426° C., 150 psig)

| Catalyst | LHSV | Conversion, % | Total Xylenes, % | Normalized Xylenes, % | | | Para-Xylene Selectivity, % |
|---|---|---|---|---|---|---|---|
| | | | | meta | para | ortho | |
| Steamed ZSM-5 (Catalyst S1) | 7 | 46.39 | 98.94 | 53.61 | 23.70 | 22.69 | 51.09 |
| | 15 | 41.58 | 99.55 | 58.42 | 23.75 | 17.84 | 57.11 |
| | 25 | 20.58 | 99.85 | 79.42 | 13.71 | 6.87 | 66.62 |
| | 32 | 9.65 | 99.92 | 90.35 | 6.32 | 3.33 | 65.49 |
| | 40 | 3.22 | 99.86 | 96.78 | 2.14 | 1.08 | 66.46 |
| | 50 | 1.24 | 99.93 | 98.76 | 0.81 | 0.43 | 65.32 |
| | 66 | 0.22 | 99.94 | 99.78 | 0.16 | 0.05 | 76.19 |
| HTC-ZSM-5 (Catalyst C1) | 7 | 45.97 | 96.16 | 54.03 | 23.19 | 22.78 | 50.45 |
| | 15 | 42.75 | 98.42 | 57.25 | 23.42 | 19.32 | 54.80 |
| | 22 | 35.08 | 99.25 | 64.92 | 22.67 | 12.42 | 64.61 |
| | 30 | 29.20 | 99.54 | 70.80 | 20.67 | 8.53 | 70.79 |
| | 40 | 6.39 | 99.89 | 93.61 | 5.19 | 1.20 | 81.22 |
| | 50 | 10.51 | 99.87 | 89.49 | 8.54 | 1.97 | 81.26 |
| | 66 | 1.83 | 99.92 | 98.17 | 1.47 | 0.37 | 79.89 |

EXAMPLE 8

A further experiment was performed for comparison purposes using a steamed ZSM-5 zeolite. The same ZSM-5 parent used in Example 7 (5 g, silica/alumina=72) was treated with flowing steam (water partial pressure=1 atm) at 450° C. for 140 hr. The resulting product catalyst 52 (alpha=10.1 silica:alumina 340 (TPAD)) was used for xylene isomerization without further modification.

Using this steamed ZSM-5 sample (1.18 g, 3 ml) under conditions identical to Example 7, meta-xylene was isomerized at varying flow rates to obtain a range of conversions. The results are given in Table 4 below and graphically in FIG. 1. FIG. 1 shows that para-selectivity rises with conversion essentially the same as the steamed ZSM-5 of Example 7.

TABLE 5

META-XYLENE ISOMERIZATION OVER ZSM-5 CATALYST

| Catalyst | LHSV | Conversion, % | Total Xylenes, % | Normalized Xylenes, % | | | Para-Xylene Selectivity, % |
|---|---|---|---|---|---|---|---|
| | | | | meta | para | ortho | |
| Steamed Pt/ZSM-5 S3 | 20 | 45.01 | 99.13 | 55.47 | 22.53 | 22.00 | 49.61 |
| | 30 | 44.26 | 93.39 | 59.69 | 21.30 | 19.02 | 44.94 |
| | 40 | 29.70 | 100.0 | 70.30 | 15.91 | 13.79 | 53.57 |
| | 60 | 26.40 | 100.0 | 73.60 | 14.82 | 11.58 | 56.14 |
| | 100 | 5.85 | 100.0 | 94.15 | 3.43 | 2.42 | 58.63 |
| HTC-ZSM-5 (Catalyst C2) | 7 | 48.05 | 97.31 | 53.39 | 23.88 | 22.73 | 48.37 |
| | 9 | 46.02 | 99.04 | 54.50 | 23.79 | 21.72 | 51.17 |
| | 11 | 44.11 | 99.52 | 56.16 | 24.17 | 19.67 | 54.52 |
| | 15 | 35.75 | 100.0 | 64.25 | 22.46 | 13.29 | 62.83 |
| | 20 | 29.71 | 100.0 | 70.28 | 20.93 | 8.79 | 70.45 |
| | 25 | 23.26 | 100.0 | 76.73 | 17.68 | 5.59 | 76.01 |
| | 30 | 18.65 | 100.0 | 81.35 | 14.71 | 3.94 | 78.87 |

TABLE 4

META-XYLENE ISOMERIZATION OVER STEAMED ZSM-5 (CATALYST S2)

| LHSV | Conversion, % | Total Xylenes, % | Normalized Xylenes, % | | | Para-Xylene Selectivity, % |
|---|---|---|---|---|---|---|
| | | | meta | para | ortho | |
| 7 | 46.13 | 98.61 | 54.50 | 23.19 | 22.30 | 50.98 |
| 15 | 39.43 | 99.50 | 60.77 | 22.10 | 17.13 | 56.33 |
| 22 | 33.63 | 99.60 | 66.37 | 20.44 | 13.19 | 60.78 |
| 26 | 9.08 | 99.75 | 91.03 | 5.65 | 3.32 | 62.99 |
| 30 | 5.81 | 99.76 | 94.40 | 3.57 | 2.03 | 63.75 |
| 35 | 1.81 | 99.76 | 98.33 | 1.00 | 0.67 | 59.88 |
| 40 | 1.21 | 99.75 | 98.91 | 0.70 | 0.40 | 63.64 |
| 66 | 0.53 | 99.78 | 99.62 | 0.20 | 0.18 | 52.63 |

EXAMPLE 9

ZSM-5 (silica:alumina=82:1) was heated to 1000° C. at 22° C. min$^{-1}$ and held at 1000° C. for 1.5 hours. The resulting product (Catalyst C2) had an alpha of 10 and a silica:alumina ratio of 282:1 (TPAD).

A sample of this zeolite (0.4 g., 1 ml) was used for meta-xylene isomerization as described in Example 7. The results are given in Table 5 below and graphically in FIG. 1 which shows that the para-selectivity of this sample follows a trend essentially identical to that of the other HTC zeolite, Catalyst C1.

A further comparison is provided by a platinum-containing xylene isomerization catalyst (catalyst 53: 50% alumina binder, 0.1 weight percent platinum, alpha=10, 0.5 g, 1 ml) which had been deactivated by steaming. Under the same isomerization conditions used in Example 7, a maximum 55% para-selectivity at 20% conversion was obtained, as shown in FIG. 1.

We claim:

1. A process for isomerizing a feedstock comprising a di-alkyl 1-substituted aromatic compound to a product containing a higher proportion of the para-di-substituted isomer, which comprises contacting the feedstock with a solid, porous catalyst comprising a crystalline aluminosilicate zeolite having a Constraint Index of 1 to 12, a silica:alumina ratio of at least 12:1 which has been heat treated to a temperature of at least 725° C. in an essentially water-free atmosphere to reduce its acidity to an alpha value below 100.

2. A process according to claim 1 in which the zeolite is heated to a temperature of 725° to 800° C.

3. A process according to claim 1 in which the zeolite is heated to a temperature of at least 800° C.

4. A process according to claim 1 in which the catalyst alpha is less than 50.

5. A process according to claim 1 in which the catalyst alpha is less than 1.

6. A process according to claim 1 in which the zeolite catalyst is ZSM-5.

7. A process according to claim 1 in which the heat treatment proceeds for at least 1 hour.

8. A process according to claim 1 in which the catalyst retains at least 55% of the crystallinity upon heat treatment.

9. A process according to claim 1 in which the heat treatment proceeds in dry air.

10. A process according to claim 1 in which the di-alkyl substituted aromatic compound comprises a xylene.

11. A process according to claim 1 in which the feedstock comprises meta-xylene and the product comprises para-xylene in an amount greater than the equilibrium amount.

12. A process according to claim 11 in which the feedstock comprises a mixture of the isomeric xylenes containing paraxylene in less than the equilibrium amount and the product comprises para-xylene in an amount greater than the equilibrium amount.

* * * * *